(12) United States Patent
Beecher et al.

(10) Patent No.: US 8,815,135 B2
(45) Date of Patent: Aug. 26, 2014

(54) PROCESS FOR THE MANUFACTURE OF UNEXPANDED GLASS-LIKE POLYSACCHARIDES

(75) Inventors: Edward Beecher, Ramsey, NJ (US); Isabelle Bolduc, Chambly (CA); Ralph Cutillo, Ramsey, NJ (US); Shuojia Dong, Montréal (CA)

(73) Assignee: Archer Daniels Midland Company, Decatur, IL (US)

( * ) Notice: Subject to any disclaimer, the term of this patent is extended or adjusted under 35 U.S.C. 154(b) by 228 days.

(21) Appl. No.: 11/765,859

(22) Filed: Jun. 20, 2007

(65) Prior Publication Data

US 2008/0125315 A1 May 29, 2008

Related U.S. Application Data

(60) Provisional application No. 60/805,287, filed on Jun. 20, 2006.

(51) Int. Cl.
*B29C 47/38* (2006.01)
*A61L 15/28* (2006.01)
*B01F 7/08* (2006.01)
*C08J 5/02* (2006.01)

(52) U.S. Cl.
CPC ............. *B01F 7/082* (2013.01); *A61L 15/28* (2013.01); *C08J 2305/00* (2013.01); *C08J 5/02* (2013.01)
USPC .............. 264/211; 264/211.11; 264/211.23

(58) Field of Classification Search
USPC ............................. 264/211.11, 211, 211.23
See application file for complete search history.

(56) References Cited

U.S. PATENT DOCUMENTS

| | | | | |
|---|---|---|---|---|
| 3,767,754 A * | 10/1973 | Manning et al. | ......... | 264/211.23 |
| 5,569,692 A * | 10/1996 | Bastioli et al. | ................. | 524/47 |
| 6,277,899 B1 * | 8/2001 | Bastioli et al. | ............... | 523/128 |
| 2004/0157532 A1* | 8/2004 | Koutlakis et al. | ............... | 451/32 |

\* cited by examiner

*Primary Examiner* — James Sanders

(57) ABSTRACT

A high-throughput process for the manufacture of absorbent unexpanded glass-like polysaccharides is disclosed. The process comprises the use of a twin screw extruder having turbulence and kneading sections, the kneading sections being located downstream from the turbulence sections.

15 Claims, 1 Drawing Sheet

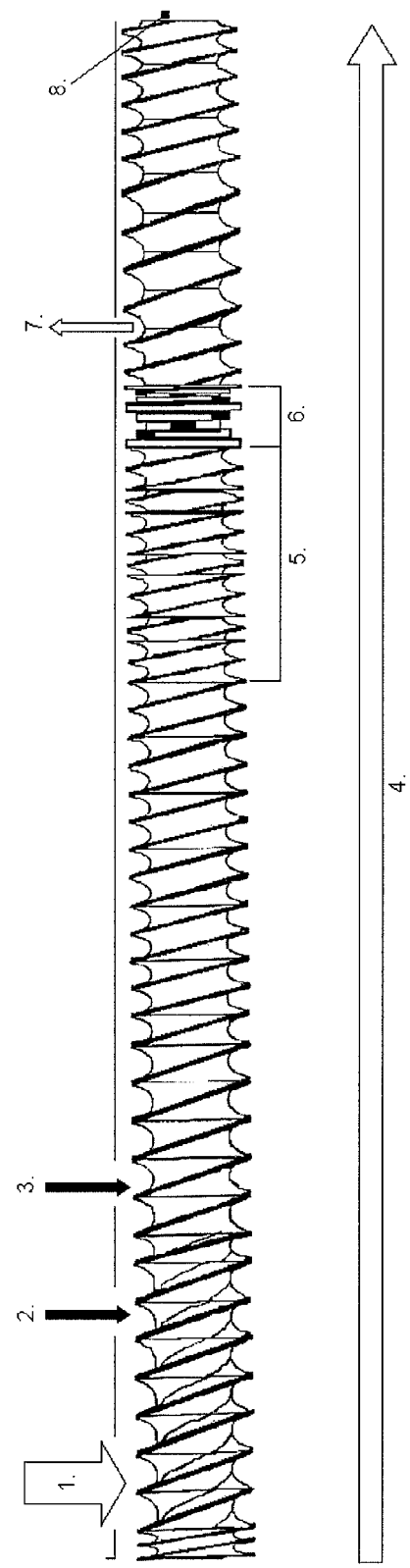

PROCESS FOR THE MANUFACTURE OF UNEXPANDED GLASS-LIKE POLYSACCHARIDES

CROSS REFERENCE TO RELATED APPLICATIONS

The present application claims the benefit of U.S. Provisional Application No. 60/805,287 filed Jun. 20, 2006, the entire contents of which are incorporated by reference.

FIELD OF THE INVENTION

The present disclosure relates to a process for the manufacture of unexpanded glass-like polysaccharides. More specifically, but not exclusively, the present disclosure relates to a process for the manufacture of unexpanded glass-like polysaccharides having absorbent properties.

BACKGROUND OF THE INVENTION

Glass-like polysaccharides comprise a class of physically modified polysaccharides. Unlike their native, crystalline counterpart, glass-like polysaccharides are substantially amorphous and comprise glass-like characteristics. Moreover, glass-like polysaccharides substantially lack an organized crystalline pattern. Glass-like polysaccharides have found use in a variety of applications. Such polysaccharides are taught as being useful for abrading surfaces.

Glass-like polysaccharides have also been described as being useful in a variety of food related applications. More specifically, they have been used to encapsulate organoleptic additives. Moreover, glass-like polysaccharides have been described as being useful as water absorbent materials.

Glass-like polysaccharides are typically produced by means of extrusion processes. A typical extrusion process comprises an extrusion vessel fitted with one or more rotating screws. The rotating screw(s) convey, pump or knead the polysaccharide along the screw to a die.

A variety of extruder configurations/designs are known in the art. A "Single Screw Extruder" (SSE) is typically characterized by an extrusion vessel fitted with one rotating screw. The screw is typically machined as a single piece. The SSE design is suitable in applications where a laminar, regular flow or low shear environment is desired. However, the SSE design is less suitable in applications typically requiring high shearing rates.

The "Twin Screw Extruder" (TSE) design is typically characterized by an extrusion vessel fitted with a pair of substantially parallel, independently rotating screws. The pair of screws may be either co-rotating or counter rotating, the co-rotating screw design being more prevalent in view of its "self-wiping" characteristics. The treaded surface defines an alternately disposed helicoidal ridge and groove. The respective treaded surfaces of a first and a second screw are intermeshed. In this way, the ridge of a first screw will typically be received by the groove of the second screw. Likewise, the groove of the first screw receives the ridge of the second screw. TSE screws typically comprise mobile block elements, each block element performing its proper function. The presence of such mobile block elements allows for a vast number of screw designs. The TSE design is suitable in applications where high shearing rates are required. However, since a TSE dissipates more shear energy compared to a SSE, it is less suitable for shear sensitive applications such as for the manufacture of unexpanded glass-like polysaccharides.

The use of extruders comprising both twin screw and single screw sections for compounding thermoplastic starch have been previously reported by Bastiolli et al. (U.S. Pat. No. 6,277,899; U.S. Pat. No. 5,874,486; U.S. Pat. No. 5,569,692; U.S. Pat. No. 5,462,982; U.S. Pat. No. 5,412,005; U.S. Pat. No. 5,384,170; U.S. Pat. No. 5,334,634; and U.S. Pat. No. 5,234,977). However, the use of high boiling plasticizers makes their removal from the final product difficult, often resulting in glass-like polysaccharides comprising a rubbery state.

The manufacture of unexpanded glass-like polysaccharides has been disclosed by Van Lengerich (U.S. Pat. No. 5,972,404; U.S. Pat. No. 6,096,363; U.S. Pat. No. 6,004,594; U.S. Pat. No. 6,436,453; U.S. Pat. No. 6,468,568; U.S. Pat. No. 6,500,463; U.S. Pat. No. 6,723,358; U.S. Pat. No. 6,190,591; U.S. App. 2002/0044968 A1). However, the glass-like polysaccharides taught by Van Lengerich were not disclosed as having any significant absorbent characteristics.

The present description refers to a number of documents, the content of which is herein incorporated by reference in their entirety.

SUMMARY OF THE INVENTION

The present disclosure broadly relates to process for the manufacture of unexpanded glass-like polysaccharides. More specifically, but not exclusively, the present disclosure relates to a process for the manufacture of unexpanded glass-like polysaccharides having absorbent properties as well as to products comprising such unexpanded glass-like polysaccharides.

In an embodiment, the present disclosure relates to a high-throughput process for the manufacture of unexpanded glass-like polysaccharides.

In an embodiment, the present disclosure relates to a high-throughput process for the manufacture of unexpanded glass-like polysaccharides having absorbent properties.

In an embodiment, the present disclosure relates to unexpanded glass-like polysaccharides having absorbent properties, the unexpanded glass-like polysaccharides being produced by the high-throughput process as disclosed herein.

In an embodiment, the present disclosure relates to compositions comprising at least one unexpanded glass-like polysaccharide having absorbent properties.

In an embodiment, the present disclosure relates to compositions comprising at least one unexpanded glass-like polysaccharide having absorbent properties and a co-absorbent material.

In an embodiment, the present disclosure relates to a process for the manufacture of unexpanded glass-like polysaccharides comprising:

(a) feeding a twin screw extruder with a polysaccharide, said extruder comprising a turbulence section and a kneading section;

(b) dispersing said polysaccharide with water to obtain a molten dispersion; and (c) extruding said dispersion through a die of a single screw extruder to obtain an unexpanded glass-like polysaccharide extrudate.

In a further embodiment, the present disclosure relates to the use of the unexpanded glass-like polysaccharides as absorbents for liquids, non-limitative examples of which include water, aqueous solutions, physiological fluids and saline solutions.

In a further embodiment, the present disclosure relates to the use of compositions comprising at least one unexpanded glass-like polysaccharide as absorbents for liquids, non-limitative examples of which include water, aqueous solutions, physiological fluids and saline solutions.

In a further embodiment, the present disclosure relates to the use of the unexpanded glass-like polysaccharides as absorbents in disposable sanitary products (i.e. diapers, incontinence articles, feminine hygiene products, airlaids and absorbent dressings), household articles, sealing materials, humectants in agricultural products for soil conditioning, in oil-drilling fluids (i.e. lost-circulation material, fracturing fluids), anti-condensation coatings, in agricultural, horticultural and forestry applications for retaining water in the soil and for the release of water to the roots of plants and trees, in the textile industry, in printing applications, in absorbent paper products, in bandages and surgical pads (i.e. wound dressings), in ore treatments, in pet litter, in water treatment, in food pads (i.e. applications related to the transportation of fresh food and food packaging), in detergents, in fire-fighting gels, in sealing materials, as chemical absorbents for the cleanup of acidic and/or basic aqueous spills including water soluble chemical spills, as polymeric gels for the slow and controlled release of cosmetics and pharmaceuticals (also known as drug delivery systems), as airlaids, and finally in the manufacture of artificial snow.

In a further embodiment, the present disclosure relates to the use of compositions comprising at least one unexpanded glass-like polysaccharide as absorbents in disposable sanitary products (i.e. diapers, incontinence articles, feminine hygiene products, airlaids and absorbent dressings), household articles, sealing materials, humectants in agricultural products for soil conditioning, in oil-drilling fluids (i.e. lost-circulation material, fracturing fluids), anti-condensation coatings, in agricultural, horticultural and forestry applications for retaining water in the soil and for the release of water to the roots of plants and trees, in the textile industry, in printing applications, in absorbent paper products, in bandages and surgical pads (i.e. wound dressings), in ore treatments, in pet litter, in water treatment, in food pads (i.e. applications related to the transportation of fresh food and food packaging), in detergents, in fire-fighting gels, in sealing materials, as chemical absorbents for the cleanup of acidic and/or basic aqueous spills including water soluble chemical spills, as polymeric gels for the slow and controlled release of cosmetics and pharmaceuticals (also known as drug delivery systems), as airlaids, and finally in the manufacture of artificial snow.

The foregoing and other objects, advantages and features of the present disclosure will become more apparent upon reading of the following non restrictive description of illustrative embodiments thereof, given by way of example only with reference to the accompanying drawings.

BRIEF DESCRIPTION OF THE DRAWINGS

In the appended drawings:
FIG. 1 is a side view of a screw design in accordance with an embodiment of the present disclosure comprising a turbulence section and a kneading section.

DETAILED DESCRIPTION OF ILLUSTRATIVE EMBODIMENTS

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

An extruder for use in processing polymeric material is typically composed of a screw, (i.e. a cylinder having one or more raised ridges (a "flight") helically disposed thereabout), which screw rotates within an annular cylinder, or barrel. The surface of the screw above which the flight(s) are raised is the root of the screw.

As used herein, the term "barrel" refers to a hollow cavity disposed within the body of an extruder, and in which one or more screws generally aligned with the barrel are disposed. A barrel is typically numbered from a feeding point located upstream the barrel to a discharge point located downstream the barrel.

As used herein, the terms "kneading element" and "kneading block" are used interchangeably and have the same meaning. Kneading elements are typically used for melting, mixing or kneading the materials that pass through the kneading zone of the extruder. To do so, kneading, elements are typically designed to enhance flow and/or shear between their periphery ridge (i.e., their outer edge) and the barrel or bore of the screw extruder as well, as between the kneading blocks themselves. This enhancement allows material to flow over the end of and between the kneading element which, in turn, allows for greater dispersion and/or distributive mixing of the material.

As used herein, the terms "turbulence element" and "turbulence block" are used interchangeably and have the same meaning. Turbulence elements typically comprise flights having a suitable turbulence causing contour. Turbulence elements cause less shear stress as compared to kneading elements.

Extruder screws can typically be described in terms of their "compression ratio". The compression ratio is related to the channel depths. The compression ratio can be calculated by dividing the depth of the channel in the first turn at the upstream end of the screw divided by the depth of the channel in the final downstream turn of the screw. For screws where the channel depth becomes shallower in the downstream direction, the compression ratio is greater than one.

Unless otherwise specified, the term "L/D ratio" refers to the barrel length (L)/barrel diameter (D) ratio.

As used herein, the term "glass-like polysaccharide" refers to an amorphous or non-crystalline polysaccharide. Glass-like polysaccharides are typically prepared by melting or heating the polysaccharide to a temperature above its glass-transition temperature followed by cooling to a temperature below its glass transition or melting point temperature. Glass-like polysaccharides are typically designated as "self-entangled" polysaccharides (see Thibodeau et al. (CA 2,462,053) and Berrada et al. (CA 2,483,049)).

As used herein, the term "polysaccharide" refers to polymers containing a backbone comprising (at least about 90%) monosaccharide repeating units and/or derivatized monosaccharide repeating units. Non-limiting examples include starches, modified starches (representative examples include carboxyalkylated starch and carboxymethyl starch), amylopectin, modified amylopectin, amylose, modified amylose, chitosan, chitin, guar gum, modified guar gum, locust bean gum, tara gum, konjac gum, konjac flour, fenugreek gum, mesquite gum, aloe mannans, cellulose, modified cellulose (representative examples include carboxyalkylated cellulose and carboxymethyl cellulose), oxidized polysaccharides, sulfated polysaccharides, cationic polysaccharides (representative examples include chitosan and guanidinated polysaccharides such as disclosed by Berrada M. (CA,2,519,018)), pectin, arabic gum, karaya gum, xanthan, kappa, iota or lambda carrageenans, agar-agar and alginates.

As used herein, the term "monosaccharide unit", refers to cyclic $C_5$-$C_6$ aldoses or ketoses. Non limitative examples of $C_5$-$C_6$ aldoses include allose, altrose, glucose, mannose, gulose, idose, galactose, talose, ribose, arabinose, xylose, lyxose. Non limitative examples of $C_5$-$C_6$ ketoses include ribulose, xylulose, fructose, sorbose and tagatose.

As used herein, the term "monosaccharide derivatives" refers to any chemically or enzymatically modified monosaccharides.

As used herein, the term "granular material", "granules", "particles", "powders", "grains" or "dusts" refers to particulate matter in a finely divided state. Granular material can include highly pulverized material with very small diameters.

As used herein, the term "Free Swell Capacity" (FSC), also called "Total Absorption", refers to the amount (g) of fluid absorbed per gram of the composition. Typical fluids are saline solutions (0.9% Weight/Weight NaCl solution, hereinafter called 0.9% NaCl solution or saline).

As used herein, the term "Centrifuge Retention Capacity" (CRC) also called "Retention", refers to the amount (g) of fluid retained per gram of the composition, following exposure of the composition to a centrifugation force of 250G. Typical fluids are saline solutions (0.9% Weight/Weight NaCl solution, hereinafter called 0.9% NaCl solution or saline).

In a broad sense, the present disclosure relates to a high-throughput process for the manufacture of unexpanded glass-like polysaccharides having absorbent properties. Surprisingly, the extrusion throughput could be increased by means of the process of the present disclosure, without adversely affecting the absorbent characteristics of the unexpanded glass-like polysaccharides produced. Glass-like polysaccharides characterized by a CRC of at least about 5.0 g/g and a FSC of at least about 7.0 g/g are obtained by means of a high-throughput extrusion process as disclosed herein.

In an embodiment of the present disclosure a polysaccharide(s) is fed into a TSE having a predetermined screw design, the screw design comprising an upstream turbulence section consisting of at least one turbulence element and a downstream kneading section consisting of at least one kneading element. Water is subsequently added in order to produce a dispersion. Alternatively, the polysaccharide may comprise a sufficiently high moisture content prior to feeding into the TSE. Heating may be applied to the TSE in order to aid in the formation of the dispersion. The product exiting the TSE (molten dispersion) is finally extruded through a die by means of a SSE to produce an unexpanded glass-like polysaccharide extrudate.

The TSE as used in the process of the present disclosure comprises a predetermined screw design. Typically, the screw design comprising an upstream turbulence section consisting of at least one turbulence element and a downstream kneading section consisting of at least one kneading element. The kneading section provides shear, mechanical energy and heat for melting and dispersing the polysaccharide. The extensive use of kneading elements should be avoided as such elements have an adverse affect on the molecular weight of the polysaccharide. It is expected that the absorbent characteristics of polysaccharides are directly linked to their molecular weight (i.e. decreased molecular weight polysaccharides having reduced absorbent characteristics).

It was unexpectedly discovered that the extensive use of kneading elements could be conveniently avoided by placing turbulence generating elements in a position located upstream relative to the kneading elements. The turbulence generating elements will bring about a gradual increase in the shearing forces as well as the frictional and mechanical energies as experienced by the polysaccharide. Moreover, the turbulence generating elements will slow the polysaccharide flow along the TSE.

In an embodiment of the present disclosure, the turbulence elements are separated by spacer elements. The spacer elements create lags and discontinuations in the polysaccharide flow, while allowing for a gradual increase in both screw fill and frictional heat. In a typical example, a turbulence section comprises at least two turbulence elements separated by a spacer element located there between.

Kneading elements are typically located downstream the turbulence elements. The kneading elements impose additional shear and mechanical energy on the polysaccharide moving along the TSE. In an embodiment of the present disclosure, a number of the kneading elements may be left-handed. The use of left-handed kneading elements increases the shear experienced by the polysaccharide moving along the TSE. Moreover, the use of such left-handed kneading elements increases the residence time of the polysaccharide within the TSE, while concomitantly increasing both screw fill and frictional energy. In an embodiment of the present disclosure, at least one kneading element is present in the screw design. In light of the present disclosure, it is well within one of ordinary skill in the art to determine further appropriate screw designs without departing from the spirit, scope and nature of present disclosure. The presence of additional shear imparting features in the kneading elements, as well as variations in the staggering angle, will further reduce the need for an excessive number of kneading elements. It is well within one of ordinary skill in the art to determine further shear imparting features as well as appropriate staggering angles without departing from the spirit, scope and nature of present disclosure.

The polysaccharide to be processed is typically fed into the TSE by means of a feeding port. In an embodiment of the present disclosure, the polysaccharide is fed into the TSE using an automated feeder. It is well within one of ordinary skill in the art to determine further appropriate feeding means without departing from the spirit, scope and nature of present disclosure.

Typically, the barrels of the TSE comprise heating zones. In an embodiment of the present disclosure, that section of the extruder barrel comprising the turbulence element(s) may be heated. Alternatively, in a further embodiment of the present disclosure, that section of the extruder barrels comprising the kneading element(s) may be heated. Alternatively, in a further embodiment of the present disclosure, the sections comprising both the turbulence and kneading element(s) may be heated. Alternatively, in a further embodiment of the present disclosure, a portion of the extruder barrels comprising the turbulence element(s) and a portion of the extruder barrel(s) comprising both the kneading element(s) may be heated. It is well within one of ordinary skill in the art to determine further appropriate heating configurations without departing from the spirit, scope and nature of present disclosure.

In an embodiment of the present disclosure, the polysaccharide to be processed comprises starch. Non-limiting examples of starches include corn, waxy corn, wheat, waxy wheat, rice, waxy rice, potato, cassava, sorghum, waxy sorghum, sago, buckwheat, beans, peas, rye, barley, and amaranth.

Starch has the physical characteristic of being insoluble in cold water. However, starch will readily disperse or melt in hot water, a behavior commonly known as gelatinization. The "gelatinous" state brings about a significant viscosity increase, demanding an increased torque output by the TSE. The increased torque output results in increased shearing forces and increased dissipated mechanical energy. The additional mechanical energy (i.e. heat) experienced by the "gelatinous" polysaccharide results in a rupture of the polymeric chains. Limiting the residence time of the polysaccharide in the TSE section of the process of the present disclosure, will reduce the amount of torque and mechanical energy experienced by the polysaccharide.

Plasticizers are typically used in the extrusion of polysaccharides. Plasticizers are added to the starches to be extruded in order to enhance material processability. In an embodiment of the present disclosure, water is used as the plasticizer. Use of an external plasticizer such as water aids in the dispersion of the polysaccharides and imparts greater melt processability. The use of water as the plasticizer has the advantage of it being more readily removed from the compositions compared to the higher boiling polyhydric plasticizers. Indeed, the glass-like polysaccharide product should be brittle and hard when being ground into a granular material. The use of low boiling plasticizers typically results in the production of an expanded glass-like polysaccharide product. Such expanded products suffers from the draw-back of yielding a finer granular material when ground.

Most polysaccharides, and especially starch, have an inherent moisture content. This moisture content, however, is generally not sufficient to achieve a desired degree of material processability. The addition of water is thus frequently required in order to produce a glass-like polysaccharide product having the desired physical characteristics. In an embodiment of the present disclosure, water is added once the polysaccharide has been fed into the TSE. This addition may be typically accomplished by the injection of water through one or more injection ports provided in the TSE. Alternatively, the polysaccharide may be mixed with water prior to being fed into the TSE. In such an embodiment, the polysaccharide is fed in the TSE as a wetted material comprising a moisture content sufficient to produce a glass-like polysaccharide product having the desired physical characteristics. The total moisture content of the polysaccharide to be extruded typically ranges from about 20% to about 30% by weight (% w/w). In an embodiment of the present specification, the total moisture content of the polysaccharide to be extruded ranges from about 23% to about 28% by weight (% w/w).

The dispersion comprising the polysaccharides is processed by a TSE having a predetermined screw design. Typically, the screw design comprises an upstream turbulence section and a downstream kneading section. In order to avoid any discharge expansion of the product at the exit of the TSE, the discharge temperature and/or the water content may be reduced. In an embodiment of the present disclosure, the barrel sections located downstream the kneading section(s) (i.e. at the exit of the TSE) are cooled. In a further embodiment of the present disclosure, the discharge temperature and/or the water content may be reduced by means of one or more venting sections located downstream the kneading section(s). A vacuum may be optionally applied to the venting sections in order to accelerate water volatilization. It is well within one of ordinary skill in the art to determine further appropriate cooling configurations without departing from the spirit, scope and nature of present disclosure.

Typically, in order to avoid additional mechanical stresses on the polysaccharide product, the TSE as used in the present disclosure does not comprise a die. The presence of a die could adversely affect the molecular weight of the polysaccharides. The polysaccharide to be processed is dispersed and molten by the TSE. Exiting the TSE, the polysaccharide product (i.e. molten dispersion) is transferred into a SSE. The transfer can be accomplished by means of simple gravity or by mechanical means. It is well within one of ordinary skill in the art to determine appropriate mechanical means without departing from the spirit, scope and nature of present disclosure. The transfer from the TSE into the SSE provides for gentle venting of the product. Optionally, additional venting may be applied to the product during the transfer.

The TSE polysaccharide product (i.e. molten dispersion) is subsequently extruded through a die or a die plate using a SSE. In an embodiment of the present disclosure, single screw extruders having a compression ratio ranging from about 1:1 to about 1:3 were used. It is well within one of ordinary skill in the art to determine appropriate SSE compression ratios and L/D ratios suitable for use without departing from the spirit, scope and nature of present disclosure. The die offers restriction to product flow thereby causing the extruder to develop the required pressure and shear. The final die also shapes the extrudate as the product exits the extruder. Since unexpanded glass-like polysaccharides do not exhibit any significant swelling at the die discharge, the extrudate size and shape is similar to that of the die openings. In embodiments of the present disclosure, die openings ranging in size from about 3 mm to about 8 mm were used. It is well within one of ordinary skill in the art to determine additional die openings without departing from the spirit, scope and nature of present disclosure.

The extrudate's temperature should not exceed 110° C. in order to avoid expansion of the glass-like polysaccharide product. The extrudate (i.e. unexpanded glass-like polysaccharide) may subsequently be cut into pellets by means of pelletizer. In an embodiment of the present disclosure, the pellets comprise a dimension ranging from about 1 mm to about 10 mm. In an embodiment of the present disclosure, the pellets comprise a dimension ranging from about 3 mm to about 8 mm. In an embodiment of the present disclosure, the pellets comprise a dimension ranging from about 1 mm to about 2 mm. Optionally, the pellets may be ground into a granular material using typical processes well known to those of ordinary skill in the art (WO 2006/074556A1). The unexpanded glass-like polysaccharide product should be brittle and hard when being ground into a granular material. The unexpanded glass-like polysaccharide product should have a moisture content not exceeding 13% (w/w) (typically associated with a glassy state) prior to being ground. In an embodiment of the present disclosure, the unexpanded glass-like polysaccharide product has a moisture content ranging from about 7% to about 9%. In an embodiment of the present disclosure, the granular material has a particle size ranging from about 150 μm to about 850 μm.

The unexpanded glass-like polysaccharide particle of the present disclosure can be employed in a variety of applications such as in disposable sanitary products (i.e. diapers, incontinence articles, feminine hygiene products, and absorbent dressings), airlaids, household articles, sealing materials, humectants (i.e. agricultural products for soil conditioning), mining and oil drilling, anti-condensation coatings, water-storing materials (agriculture/horticulture/forestry), absorbent paper products, surgical absorbents, pet litter, bandages, wound dressings, chemical absorbents, polymeric gels for cosmetics and pharmaceuticals, artificial snow, in firefighting techniques, and in applications related to the transportation of fresh food or seafood, as well as in food packaging applications. Moreover, the unexpanded glass-like polysaccharide particles of the present disclosure can be employed to absorb a variety of liquids, non-limiting examples of which include physiological fluids, saline solutions, water and aqueous solutions.

The unexpanded glass-like polysaccharide particles of the present disclosure can be mixed with other co-absorbent materials. In an embodiment of the present disclosure, the compositions comprise from about 1 to about 99% (w/w) of unexpanded glass-like polysaccharides, and from about 99 to about 1% (w/w) of co-absorbent material. Non-limiting examples of co-absorbent materials include synthetic superabsorbent polymers, mannose-based polysaccharides, ionic polysaccharides, fibers and mixtures thereof.

In an embodiment of the present disclosure, absorbent compositions are prepared by mixing the unexpanded glass-like polysaccharide particles with ionic polysaccharides, either cationic or anionic polysaccharides, or mixtures thereof. In a further embodiment, absorbent compositions are prepared by mixing the unexpanded glass-like polysaccharide particles with one or more anionic polysaccharides.

Non-limiting examples of anionic polysaccharides include carboxyalkyl polysaccharides, carboxymethyl cellulose, carboxymethyl starch, oxidized polysaccharides, xanthan, carrageenans, pectin and mixtures thereof.

Non-limiting examples of fibers include cellulose, viscose, rayon, cellulose acetate, Nylon™, polyalkylenes, polyethylene, polypropylene, bi-component fibers, polyesters, polylactides, polypropanediols, Lyocell™, sphagnum and mixtures thereof.

Non-limiting examples of mannose based polysaccharides include guar, tara, locust bean, konjac, fenugreek extracts, mesquite extracts, aloe mannans and mixtures thereof.

The co-absorbent synthetic superabsorbent polymers can generally be obtained via the polymerization of monomers, non-limiting examples of which include acrylic acid, acrylate salts, acrylic ester, acrylic anhydride, methacrylic acid, methacrylate salts, methacrylic esters, methacrylic anhydride, maleic anhydride, maleic salts, maleate esters, acrylamide, acrylonitrile, vinyl alcohol, vinyl pyrrolidone, vinyl acetate, vinyl guanidine, aspartic acid, aspartic salts and mixtures thereof.

EXPERIMENTAL

Materials

Corn starch was obtained from Cargill® (Minneapolis, Minn., USA).

TSE/SSE Combination

Unexpanded glass-like polysaccharides were manufactured using a ZSK Megacompounder semi-industrial twin screw extruder having a 58 mm screw diameter from Coperion (Ramsey, N.J., USA). A TSE screw design comprising both turbulence and kneading sections is illustrated in FIG. 1. The polysaccharide to be extruded is fed into the TSE by means of an injection port 1. TSE injection ports 2 and 3 provide for the addition of water. The extrusion flow transports the polysaccharide through a turbulence section 5 followed by a kneading section 6 located further downstream. The direction of travel of the polysaccharide (i.e. the extrusion flow 4), as it is transported away from the injection port 1 by the screw, is considered the "downstream" direction. A venting port 7 located downstream the kneading section 5 provides for the discharge temperature and/or the water content of the molten dispersion to be reduced. The molten dispersion exits the TSE through exit port 8 from where it is transferred to a SSE (not shown). An embodiment of a TSE screw design is shown hereinbelow in Table 1.

TABLE 1

TSE Screw design

| Extrusion Flow | Number of elements | Pitch length (mm) | Element length (mm) | Staggering angle | Element Name |
|---|---|---|---|---|---|
| Beginning | 1 | 40 | 40 | | 040/040-34 |
| | 7 | 110 | 55 | | 110/055-34SK |
| | 1 | 80 | 40 | | 080/040-38-SK-N |
| | 5 | 110 | 55 | | 110/055-34 |
| | 1 | 80 | 40 | | 080/040-34 |
| | 6 | 80 | 80 | | 080/080-34 |
| | 1 | 60 | 60 | | 060/060-34 |
| | 1 | — | 1 | | 000/001-34 |
| | 1 | 60 | 30 | | 060/030-34 |
| | 1 | — | 1 | | 000/001-34 |
| | 1 | 60 | 60 | | 060/060-34 |
| | 1 | — | 1 | | 000/001-34 |
| | 1 | 60 | 30 | | 060/030-34 |
| | 1 | — | 1 | | 000/001-34 |
| | 1 | 60 | 60 | | 060/060-34 |
| | 1 | — | 1 | | 000/001-34 |
| | 1 | 60 | 30 | | 060/030-34 |
| | 1 | — | 1 | | 000/001-34 |
| | 1 | 60 | 60 | | 060/060-34 |
| | 1 (comprising 5 lobes) | — | 12 (for each lobe) | 45 | KB 45/5/60 |
| | 1 (comprising 5 lobes) | — | 6 (for each lobe) | 45 | KB 45/5/30 LH |
| | 1 | 80 | 80 | | 080/080-34 |
| Exit Port | 4 | 110 | 55 | | 110/005-34 |
| | 2 | 80 | 80 | | 080/080-34 |
| | 1 | 60 | 60 | | 060/060-34 |

The TSE screw as described hereinabove in Table 1 has an L/D ratio of 38. The screw was comprised of 9 barrel segments of equal length. The polysaccharide (i.e. starch) was fed into the TSE by means of an injection port 1 located in barrel segment 1 of the screw. Water was injected by means of injection ports 2 and 3 located in barrel segments 2 and 3 of the screw. The TSE did not comprise a die. The polysaccharide product (i.e. molten dispersion) was transferred into a Coperion SSE having a 150 mm screw diameter, a compression ratio of 1:2 and an L/D ratio of 8, by means of simple gravity. The SSE was comprised of a die plate having die openings of about 3 mm (320 openings). The die was equipped with an EGR hot face eccentric rotary knife pelletizer (Coperion), positioned at die plate discharge surface.

Grinder

A Braun™ model KSM coffee grinder was used to grind the extruded samples.

Sieve Shaker

When indicated, samples were sieved using a Tyler Rota-Tap™ test sieve shaker

Test Methods

As discussed in Modern Superabsorbent Polymer Technology (Buchholz, F. L. and Graham, A. T. Eds., Wiley-VCH, New York, 1998, section 4.6.1. Swelling Capacity: Theory and Practice, p. 147), several measurement methods are used in order to characterize the swelling capacity of a polymer. In the field of superabsorbents, the Gravimetric Swelling Capacity [also called the Free Swell Capacity (FSC)] and the Centrifuge Capacity [also called the Centrifuge Retention Capacity (CRC)] are recommended methods. The FSC and the CRC were used to compare the swelling capacities of the obtained absorbent products.

Tea Bags for FSC and CRC Measurements

Tea bags (10×10 cm) were made from heat sealable Ahistrom™ filter paper (16.5±0.5 g/m$^2$).

FSC Measurements

The Free Swell Capacity (FSC) in a 0.9% NaCl solution was determined according to the recommended test method 440.2-02 from EDANA (0.5 g of product in tea bag).

CRC Measurements

The Centrifuge Retention Capacity (CRC) in a 0.9% NaCl solution was determined according to the recommended test method 441.2-02 from EDANA (0.5 g of product in tea bag).

Example

Twin Screw Extrusion

Single Screw Extrusion

Corn starch having a moisture content of about 10.0% (w/w) was fed into a TSE (ZSK 58 mm) by means of a gravimetric feeder at a rate of 545 kg/hr (1200 lbs/hr). Water was subsequently injected (injection ports 2 and 3 located in barrel segments 2 and 3) into the TSE at a rate of 120 kg/hr (264 lbs/hr) such that the water content of the starch was increased to about 26%. The extruder had the following barrel temperature profile: $Tb_2=32°$ C., $Tb_3=31°$ C., $Tb_4=34°$ C., $Tb_5=49°$ C., $Tb_6=70°$ C., $Tb_7=95°$ C., $Tb_8=101°$ C. and $Tb_9=96°$ C. The extruder screw was rotating at 340 rpm and the pressure at the discharge port was measured to be 482 kPa (70 Psig) (without the presence of a die). The product (i.e. molten dispersion) having a temperature of 114° C. and a moisture content of 22.3% was transferred by gravity into a Coperion SSE. The SSE had the following barrel temperature profile: $Z_1=97°$ C. and $Z_2=77°$ C. (both zones being equidistant). The extruder screw was rotating at 28 rpm and the pressure at the die plate discharge was measured to be 4447 kPa (645 Psig). The unexpanded glass-like starch, at the exit of the die discharge plate, had a temperature of 105° C. The product was subsequently cut into pellets, died using a fluidized bed drier and finally ground into a granular material. The granular material had the following particle size distribution: particles ranging from about 246 μm to 589 μm (80% w/w); and particles ranging from about 147 μm to 246 μm (20% w/w). The Free Swell Capacity (FSC) and Centrifuge Retention Capacity (CRC) were measured to be of the order of 7.3 g/g and 5.4 g/g respectively.

It is to be understood that the disclosure is not limited in its application to the details of construction and parts illustrated in the accompanying drawings and described hereinabove. The disclosure is capable of other embodiments and of being practiced in various ways. It is also to be understood that the phraseology or terminology used herein is for the purpose of description and not limitation. Hence, although the present disclosure has been described hereinabove by way of illustrative embodiments thereof, it can be modified, without departing from the spirit, scope and nature of the disclosure as defined in the appended claims.

What is claimed is:

1. A process for the manufacture of unexpanded glass-like polysaccharides, comprising:
    a) feeding a twin screw extruder with a polysaccharide and a plasticizer of water, said extruder comprising a turbulence section and a kneading section, wherein said kneading section is located downstream of said turbulence section, and wherein said turbulence and kneading sections apply shearing forces on said polysaccharide, and wherein said twin screw extruder does not comprise a die;
    b) dispersing said polysaccharide with water to obtain a molten dispersion;
    c) transferring said molten dispersion from said twin screw extruder to a single screw extruder, wherein said transferring step decreases water content in said molten dispersion; and
    d) extruding said molten dispersion with said single screw extruder that does comprise a die to obtain an unexpanded glass-like polysaccharide extrudate, wherein said extrudate is at a temperature that does not exceed about 110° C. at an exit of said die.

2. The process of claim 1, wherein the polysaccharide is starch.

3. The process of claim 2, wherein the starch is selected from the group consisting of corn, waxy corn, wheat, waxy wheat, rice, waxy rice, potato, cassava, sorghum, waxy sorghum, sago, buckwheat, beans, peas, rye, barley, and amaranth.

4. The process of claim 1, wherein said polysaccharide comprises a moisture content ranging from about 20% to about 30% (w/w).

5. The process of claim 1, wherein said polysaccharide comprises a moisture content ranging from about 23% to about 28% (w/w).

6. The process of claim 1, wherein further comprising the step of venting the molten dispersion with vents located downstream the kneading section[s].

7. The process of claim 1, wherein the single screw extruder comprises a compression ratio ranging from about 1:1 to about 1:3.

8. The process of claim 1, wherein the single screw extruder comprises a L/D ratio ranging from about 8 to about 15.

9. The process of claim 7, wherein the single screw extruder comprises a L/D ration ranging from about 8 to about 15.

10. The process of claim 1, where said turbulence section comprises a screw flight comprising a turbulence causing contour.

11. The process of claim 1, wherein said turbulence section causes less shear than the kneading section.

12. The process of claim 1, wherein said turbulence section comprises turbulence blocks separated by spacers.

13. The process of claim 1, further comprising drying and grinding said unexpanded glass-like polysaccharide into particles that are characterized with a FSC of at least 7 g/g and a CRC of at least 5 g/g.

14. The process of claim 1, wherein said transferring step is done by gravity.

15. The process of claim 1, wherein said transferring step is done by a mechanical means.

* * * * *